United States Patent
Bouet et al.

(10) Patent No.: US 7,825,348 B2
(45) Date of Patent: Nov. 2, 2010

(54) METHOD OF REPAIRING A BLADE OF A ONE-PIECE BLADED DISC OF A TURBOMACHINE AND TEST PIECE FOR IMPLEMENTING THE METHOD

(75) Inventors: Bernard Bouet, Gretz Armainvilliers (FR); Stephane Kerneis, Velizy (FR); Claude Andre Charles Pagnon, Vaux sur Mer (FR); Eric Christian Jean Pinto, Fleury en Biere (FR)

(73) Assignees: SNECMA, Paris (FR); SNECMA Services, Paris (FR)

( * ) Notice: Subject to any disclaimer, the term of this patent is extended or adjusted under 35 U.S.C. 154(b) by 1142 days.

(21) Appl. No.: 11/457,992

(22) Filed: Jul. 17, 2006

(65) Prior Publication Data
US 2007/0023485 A1    Feb. 1, 2007

(30) Foreign Application Priority Data
Jul. 29, 2005    (FR) .................................. 05 08151

(51) Int. Cl.
*B23K 26/20*    (2006.01)
*B23P 6/00*    (2006.01)
*B23P 15/00*    (2006.01)

(52) U.S. Cl. ........................... 219/121.14; 219/121.64; 228/119; 29/889.1; 29/889.7

(58) Field of Classification Search ............ 219/121.13, 219/121.14, 121.35, 121.63, 121.64, 121.85; 228/119, 57; 29/889.1, 889.7–889.722
See application file for complete search history.

(56) References Cited

U.S. PATENT DOCUMENTS

| | | | |
|---|---|---|---|
| 3,918,928 A | * | 11/1975 | Kiyonaga et al. ............ 428/684 |
| 4,224,501 A | * | 9/1980 | Lindbom et al. ....... 219/124.34 |
| 4,364,113 A | * | 12/1982 | Sengebusch et al. .......... 702/34 |
| 4,409,462 A | | 10/1983 | Jahnke |
| 4,730,093 A | | 3/1988 | Mehta et al. |
| 5,026,967 A | * | 6/1991 | Bell et al. ............... 219/121.64 |
| 5,038,619 A | * | 8/1991 | Hueck ......................... 73/810 |
| 5,448,164 A | * | 9/1995 | Selley et al. ............. 324/158.1 |
| 5,795,412 A | | 8/1998 | Delmaire |
| 5,814,783 A | * | 9/1998 | Harville et al. ............. 219/110 |
| 6,077,615 A | * | 6/2000 | Yada et al. .................. 428/544 |
| 6,238,187 B1 | | 5/2001 | Dulaney et al. |

(Continued)

FOREIGN PATENT DOCUMENTS

JP    2566544 B2 *    7/1987

(Continued)

*Primary Examiner*—Samuel M Heinrich
(74) *Attorney, Agent, or Firm*—Oblon, Spivak, McClelland, Maier & Neustadt, L.L.P.

(57) ABSTRACT

To repair the blade, a patch is welded by an electron beam. The method starts by machining the damaged zone so as to obtain a zone to be repaired having a defined profile; welded on to a first test piece element corresponding to the blade, having said defined profile, is a second test piece element, corresponding to the patch, in order to obtain a start-of-run test piece; the quality of this test piece is verified and, if it corresponds to the repair acceptance criteria, the patch is welded on to the zone to be repaired using the same electron-beam welding machine without changing its operating parameters, and the repaired zone is reworked by machining.

18 Claims, 3 Drawing Sheets

U.S. PATENT DOCUMENTS

| | | |
|---|---|---|
| 6,568,077 B1 | 5/2003 | Hellemann et al. |
| 6,701,615 B2 * | 3/2004 | Harding et al. ............ 29/889.1 |
| 6,767,649 B2 * | 7/2004 | Staubli et al. ............... 428/553 |
| 2006/0193612 A1 | 8/2006 | Bouet et al. |
| 2008/0000947 A1 | 1/2008 | Derrien et al. |

FOREIGN PATENT DOCUMENTS

| | | | |
|---|---|---|---|
| JP | 404100687 A | * | 4/1992 |

* cited by examiner

METHOD OF REPAIRING A BLADE OF A ONE-PIECE BLADED DISC OF A TURBOMACHINE AND TEST PIECE FOR IMPLEMENTING THE METHOD

The invention relates to a method of repairing a one-piece rotor blade of a turbomachine, and to a start-of-run, end-of-run or development test piece element for implementing the method.

A turbojet comprises several rotors, which rotate about their axes. These rotors may include a disc, with a rim along which the blades are fitted. Conventionally, the blades are retained by their root in a housing provided for this purpose. To meet the increased performance requirements of engines, these rotors may now be one-piece rotors, referred to as one-piece bladed discs, called "blisks". In a blisk, the blades and the disc form only a single part. For this purpose, a forged blank is machined so as to form the disc, the blades extending radially around its circumference, while still being a one-piece component. It is also possible to weld certain parts, the resulting blisk being a one-piece component. There are many advantages of one-piece rotors, especially in terms of mass.

Because of ingestion of foreign bodies into the engine, or due to erosion caused by dust or particles entrained by the flow of the gas stream, the blades may have damaged regions, in the form of wear or torn-off portions, which impair the efficiency of the turbojet. The regions involved are generally the tip, the corner on the leading edge or the trailing edge side, and the leading edge or trailing edge. To repair the blades in a blisk is not easy, as it is not possible for them to be removed in order to repair them.

The wear or damage, if it cannot be repaired, results in the defective part being replaced. Now, in the case of a blisk, the replacement of a blade involves replacing the entire blisk.

Document U.S. Pat. No. 6,238,187 teaches a method of repairing the blades. In this method, a portion of the blade around the damaged region is cut out, said portion being standardized so as to make the method reproducible whatever the shape and size of the damaged region, as long as it lies within the portion in question. A replacement part, commonly referred to as a patch, is then welded on to the blade. This patch has dimensions larger than those of the portion of the blade removed and is then machined so as to return to the initial shape of the blade.

Document U.S. Pat. No. 6,568,077 teaches the use, for the step of welding a patch in the above method, of an electron-beam welding method that has the advantages of a high welding rate and of its ability to be able to weld large thicknesses.

However, a problem arises in the case of rotors made of a titanium alloy called Ti17. This alloy is mentioned, for example in the Applicant's Patent Application EP 1 340 832, which relates to a product, such as a blade, made of this material, which is difficult to weld because, when it melts, gas evolution occurs during welding giving rise to micropores or blowholes in the heat-affected zone (HAZ) that result in a reduction in the mechanical properties of the welded part. This reduction may be up to 80% in the case of the mechanical strength. Such a reduction cannot be tolerated in aeronautical applications and occurs in the case of electron-beam welding. Moreover, in the case of a Ti17 rotor, TIG or microplasma techniques conventionally used and common practice in the aeronautical industry fail to provide acceptable results.

In addition, recent blades have complex three-dimensional shapes, the thickness of their walls being variable, and make it difficult to use an electron-beam welding method, which requires very precise definition of the parameters. These parameters must be defined for each situation in question, any standardization being difficult to achieve.

The object of the invention is to propose a method of repairing a blade of a one-piece rotor of progressively varying shape and variable thickness, said method including an electron-beam welding step.

The invention relates to a method of repairing a blade of a one-piece bladed disc of a turbomachine that includes at least one damaged region, by the electron-beam welding of a patch by means of an electron-beam welding machine, comprising the steps of preparing the damaged region, of electron-beam welding the patch and reworking of the repaired region by machining, characterized in that:

the preparation step comprises the machining of the damaged region so as to obtain a region to be repaired of defined profile;

the welding is carried out, on a first test piece element, corresponding to the blade, having said defined profile, with the welding machine, the operating parameters of which are preset, and of a second test piece element, corresponding to the patch, having the characteristics of the patch, in order to obtain what is called a "start-of-run" test piece;

the quality of the start-of-run test piece after welding is checked and, if the quality of the test piece corresponds to the repair acceptance criteria, the patch is welded on to the region to be repaired with the same electron-beam welding machine without changing the operating parameters thereof; and the repaired region is reworked by machining.

The present invention has the advantage of repairing one-piece bladed discs on an industrial scale, by being based on the capability of controlling electron-beam welding machines. Once the machine has been validated and the parameters set, all that is required is to check, by the prior welding of the second test piece element, corresponding to the patch, onto the first test piece element, having the profile of the blade, that the parameters are correct and have not drifted. Surprisingly, it has been found that this method allows great reliability to be achieved in repairing components as complex as blisks. The prior check is sufficient for authorizing a number of blades on the same disc to be repaired.

According to another feature, and to ensure in a complementary manner that the operation has been correctly carried out, the method includes, after the patch has been welded on to the blade or the patches on to the successive blades to be repaired, a step of welding, on to a first test piece element, corresponding to the blade, having the defined profile of the blade, a second test piece element, corresponding to the patch, having the characteristics of the patch, with the same electron-beam welding machine without changing the operating parameters thereof, in order to obtain what is called an "end-of-run" test piece, and a step of checking the quality of the end-of-run test piece.

This step has the benefit of providing a state of execution of the welding method at the end of a run, when the parameters of the installation may have drifted slightly. If the end-of-run test piece is of an acceptable quality, it is then concluded from this that all of the repairs that were made between the welding of the start-of-run test piece and the welding of the end-of-run test piece were performed correctly. This makes it possible, on the one hand to simplify the repair methods and, on the other hand, to save carrying out direct quality checks on the blisk which, because of the space constraints of the latter, are not easy, or even impossible to implement.

The method is particularly suitable when the constituent material of the disc is a titanium alloy, especially Ti17, but the Applicant does not mean to limit the scope of its rights to just this application.

The method applies to at least one region to be repaired from among the aerofoil tips, leading edge or trailing edge corners and the leading or trailing edges.

According to another feature, the method of repairing a one-piece bladed disc includes a step of developing the electron-beam welding machine, during which the parameters are preset by the welding, on to a first test piece element, corresponding to the blade, having the defined profile of the blade of a second test piece element, corresponding to the patch, having the characteristics of the patch, in order to obtain what is called a "development test piece" followed by non-destructive and/or destructive testing of the development test piece.

Preferably, the first elements, and the second elements of the start-of-run test piece, of the end-of-run test piece and the development test piece are identical.

According to another feature, the repair method also includes a step of validating the material/machine pair, during which two plates of the material of the blade, with a thickness at least equal to the maximum thickness of the defined profile of the blade, are welded in order to obtain a test piece for validating the mechanical integrity, and at least cyclic fatigue tests are carried out on the test piece for validating the mechanical integrity.

The invention also relates to a start-of-run, end-of-run or development test piece for implementing the method.

The invention will be more clearly understood with the aid of the following description of the preferred form of implementation of the method of the invention, with reference to the appended plates in which.

Figure 1:
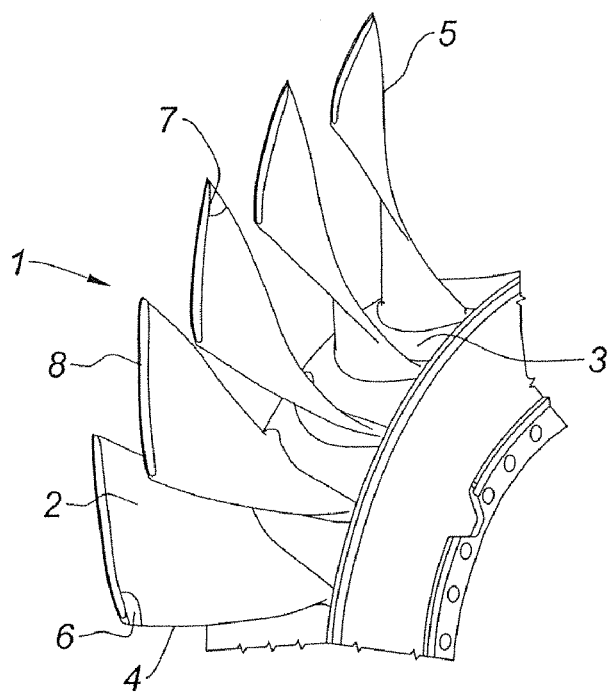
FIG. 1 shows a perspective partial view of a one-piece bladed disc, one blade of which may be repaired using the method of the invention.

Referring to FIG. 1, the method of the invention relates to the repair of a blade 2, extending radially on the periphery of a rim 3 of a one-piece bladed disc 1 (blisk 1), here made of Ti17 titanium. Because of an impact or of wear, this blade has a damaged region. The regions liable to be damaged are the leading edge 4, the trailing edge 5, the leading edge corner 6, the trailing edge corner 7 and the line of the tip 8 of the blade, here provided with a thinned portion forming, in a known manner, the sealing lip.

Figure 2:
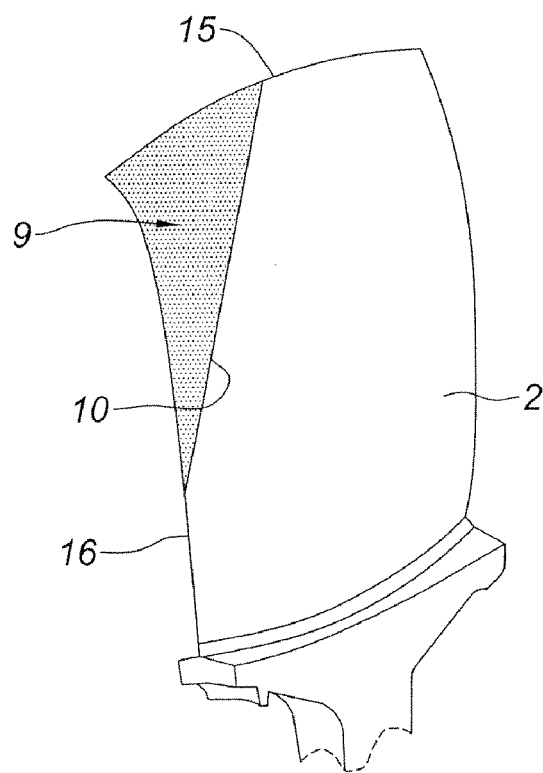
FIG. 2 shows schematic perspective view of one blade of the disc of FIG. 1, showing, in grey, the blade portion removed during the preparation phase of the method of the invention.

Predefined on the blade are standardized portions in which the damaged regions that can be repaired are located, these portions corresponding to blade portions which are cut out in order to be replaced. A first step of the method consists in checking whether the damaged region of the blade lies in such a portion. FIG. 2 shows a blade 2 and such a standardized portion 9, shown in grey. This portion 9 here includes the leading edge corner of the blade 2.

Figure 3:
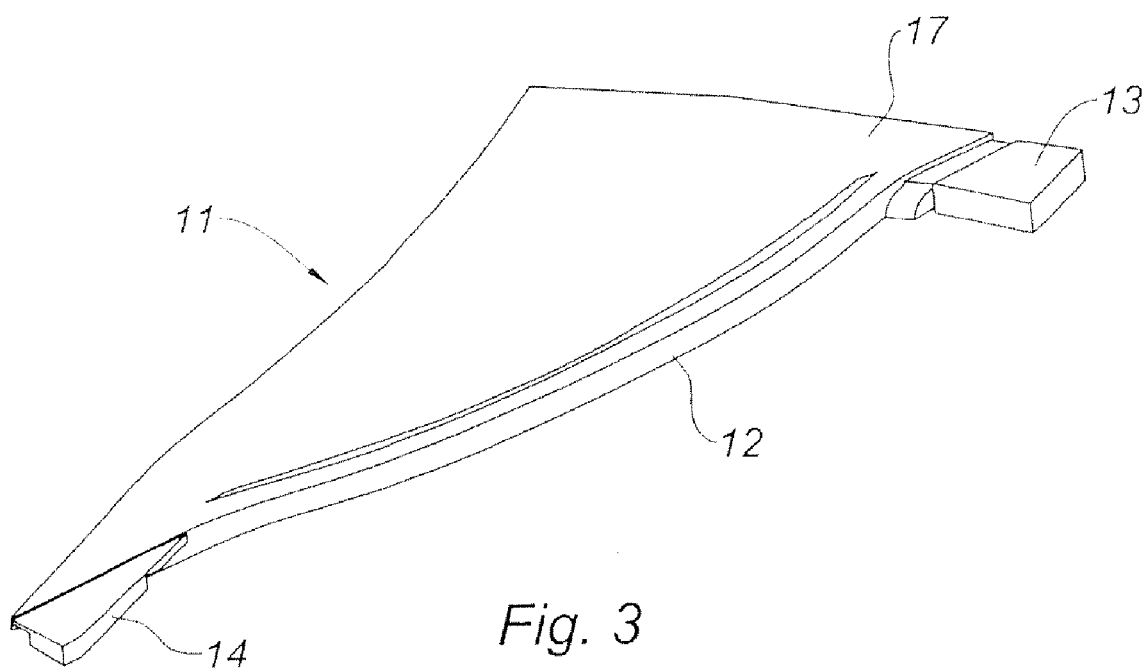
FIG. 3 shows a schematic perspective view of a patch with heels for implementing the method of the invention.

If such is the case, the standardized portion is cut out by machine. The parameters for this machining operation are preset and identical for blades of any one type. The cutting line 10 of the standardized portion 9 is defined so as, on the one hand, to vary as slowly as possible so as not to have excessively abrupt points of inflection or corners, so as to make the cutting and subsequent welding easier, and, on the other hand, to extend into a region of the blade where the operating stresses are minimal, or at the least not maximal, so that the zone that will be welded shall not be subsequently subjected, along the weld line, to excessively high stresses. The maximum dimensions of the cut-out portion are defined according to the use of the engine and taking into account the aerodynamic loads undergone by the blade 2. The defects in a blade 2 that are contained in such a portion 9, whatever their shape or their nature, may be repaired by cutting out this portion 9 and replacing it with a standardized patch 11, which may be seen in FIG. 3, and will be described later. The cutting operation is also carried out so as to guarantee a surface finish compatible with the desired welding quality.

What is thus obtained on the blade 2 is a cutting line having a defined profile.

Once this cutting has been carried out by machining, the blade 2 and especially its cutting line 10, is cleaned so as to prepare it for the welding step.

Figure 4:
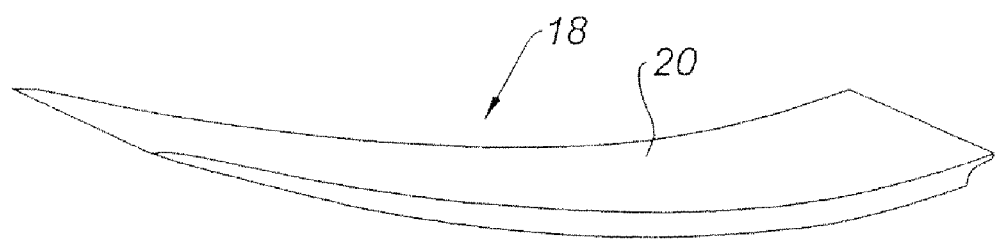
FIG. 4 shows a schematic perspective view of the first test element of the start-of-run or end-of-run or development test piece for implementing the method of the invention, corresponding to a blade.
Figure 5:
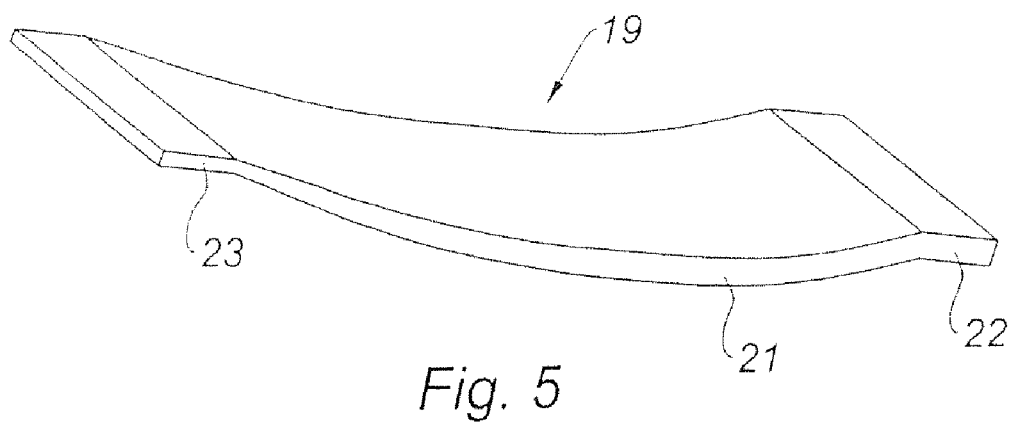
FIG. 5 shows a schematic perspective view of the second test piece element of the start-of-run or end-of-run or development test piece for implementing the method of the invention, corresponding to a patch.

Before welding a patch 11 on to the cut blade, a start-of-run test piece is welded, the first element and the second element of which may be seen in FIGS. 4 and 5, which will be explained in detail later.

The patch 11 is then brought into contact with the cutting line 10 of the blade 2. This contacting operation is performed by a device for holding the blade 2 and the patch 11 in place. This device, which is not described here, must be designed so as to allow very precise positioning of these elements with respect to each other and is adapted to each blade 2. Preferably, the same device is used for holding the blade 2 in place while its standardized portion 9 is being cut off. This makes it possible to retain the same parameters and to have a welding plane identical to the cutting plane.

The patch 11, which is made of the same material as the blade, here Ti17 titanium, has a profile along a cutting line 12 that exactly repeats the defined profile of the cutting line of the blade 2 and has a thickness oversize with respect to the thickness of the blade, here approximately 1 mm, divided at 0.5 mm on one side of the blade and 0.5 mm on the other side, for a blade whose thickness varies between 0.5 and 6 mm, preferably between 0.7 and 3.45 mm. The thickness of the patch 11 thus follows, along its cutting line 12 but also over its entire area, the variations of the profile and the variable thickness of the blade, along its cutting line 10 and over the area corresponding to the portion that has been removed, with a thickness oversize. In other words, the surface shape of the patch 11 corresponds overall to the surface of the portion 9 of the blade 2 that has been cut out, its dimensions being slightly greater.

In the extension of each end of its cutting line 12, the patch 11 has a heel 13, 14, projecting from the surface of the cutting line 12 and extending so as not to interfere with the blade 2 once the patch 11 has been brought into contact with the latter. More precisely, each heel 13, 14 matches the shape of the edge 15, 16 of the blade 2 that extends from its cutting line 10, in this case the edges corresponding to its tip line 15 and its leading edge 16, which would form the leading edge corner of the blade 2. These heels 13, 14 are used to initiate and terminate the welding, as will be seen later. The heels 13, 14 may be formed from a single part with the patch 11 or attached thereto. If they are made as one part with the patch, they may also allow an operator to take hold of the patch 11 and move it. Heels could also be attached to the blade 2.

The cutting line 12 of the patch 11 is therefore brought into contact with the cutting line 10 of the blade 2, this contacting operation having to be carried out very precisely, by means of the abovementioned holding device, so that the profile of the patch 11 exactly follows the profile of the blade 2, something which was not the case in the prior art where the patch is a constant thickness substantially greater than the maximum thickness of the blade. Thanks to this varying thickness of the patch 11, excessively large differences and thickness variations between the blade 2 and the patch 11 are avoided, thereby simplifying the subsequent electron-beam welding process and guaranteeing better quality thereof, which process rightly requires to be executed very precisely. This makes it possible to limit the causes of welding defects. The holding device, which holds the blade 2, the patch 11 and possibly the heels 13, 14 in place, if these are not integral with the patch 11, must therefore be able to be positioned in three dimensions.

The electron-beam welding then takes place by means of an electron-beam welding machine. For this purpose, the blade 2 and patch 11 assembly is placed in an inert atmosphere, typically in a vacuum, and an electron gun of the machine fires an electron beam on to the weld bead, located at the interface between the cutting lines 10, 12 of the blade 2 and of the patch 11, the kinetic energy of the electrons heating the workpieces and allowing them to be welded together. The various parameters of this welding step, especially the beam power (typically between 50 and 200 kW), the electron velocity set by the acceleration voltages, the electron density, the focusing current, allowing the depth of the focal point to be adjusted, the amplitude, form and frequency of the vibration of the electron beam around its axis, and the speed of displacement of the beam, are defined beforehand by means of trials on development test pieces similar to the start-of-run test piece, which will be explained later.

The advantages of using electron-beam welding are especially the welding speed and the quality of the welding obtained along a relatively narrow weld bead.

The welding is started on a heel 13, since, in electron-beam welding, the start of welding generates defects in the workpiece, and also a hole. These drawbacks do not affect the blade 2 insofar as they are confined to the heel 13. Moreover, starting the welding on the heel 13 makes it possible, when the electron beam reaches the joint plane between the blade 2 and the patch 11, for the electron gun to be at full power, which power is maintained until the end of the cutting line 10 of the blade 2. The entire operation of welding the patch 11 to the blade 2 is therefore carried out, as regards the cutting line 10 of the blade 2, in the "steady state" of the electron gun. It may be noted that in the particular case in question, the weld bead is of the open-ended type. The welding continues and terminates on the opposite heel 14, so that the defects and the hole, which are also generated in this phase, are confined to this heel 14.

The electron beam is not directed exactly on to the joint plane but slightly offset to the side of the patch 11, since, around a weld bead an "undercut" may appear, that is to say a zone in which the thickness is reduced relative to its initial thickness, owing to the loss of material towards the weld bead. Since the patch 11 has a greater thickness than the blade 2, the material has a tendency to go beyond the weld bead so as to fill the undercut on the blade 2 side. The undercut, which could form on the patch 11 side could disappear in the machining step that follows. The offset of the beam on the patch 11 side therefore prevents an undercut being formed in the repaired blade 2.

The parameters of the electron-beam welding machine are preferably refined by means for slaving these parameters to the geometry of the weld bead, and therefore to the geometry of the cutting line 10 of the blade 2, in a progressive manner, in real time, along this cutting line 10. The weld bead obtained is thus of better quality.

Another advantage of using heels 13, 14 should be noted. The blade 2 includes, along its tip line 15, a sealing lip corresponding to a lip 17 on the patch 11. Owing to its very small thickness, this lip cannot be directly electron-beam welded, as this zone would collapse during welding. It is therefore frequent, in the prior art, not to weld the lip but to form a lip by a subsequent build-up process, for example, using a laser, which increases the costs appreciably. The heel 13, placed beneath the lip 10 on the side of the blade 2 and of the patch 11 where the continuation of the profile is wider, forms a thickness oversize at the lip. Thus, the region where the lip portions are welded together is not too thin and these portions may be welded by electron-beam welding so as to ensure continuity of the lip of the blade 2 once repaired.

Once the electron-beam welding operation has been carried out, the blade 2, with the welded patch 11, undergoes a heat treatment so as to reduce the tensile stresses generated during welding. An ultrasonic peening operation may also be carried out. Certain checks are performed so as to ensure quality of the welding. These checks may amount to visual checks for verifying that the welding has taken place properly and has not, in principle, produced appreciable imperfections, owing to the guarantees afforded by the welding of a start-of-run test piece. For this purpose, the aim may be to visually check for traces of oxidation, which could be due to poor shielding by the confinement gas, any lack of bonding, cracks (under a binocular microscope) and unfused material.

If according to this or these summary checks, the result is satisfactory, the patch 11 is then machined so as to remove the surplus material in order to recover an almost definitive shape, practically corresponding to the shape of the complete blade 2. Several passes of the machining tool are made, little material being removed each time, until the blade whose dimensions are slightly greater than the final dimensions, that is to say the dimensions corresponding to the initial blade, is obtained. These are the dimensions of the portion 9 that has been cut out and replaced by the patch 11, the rest of the blade 2 not being machined since it must remain identical to the rest of the initial blade 2.

The repair of the blade 2 is refined and completed by manual polishing, so as to obtain a blade 2 identical to the initial blade 2.

The method of the invention is especially characterized by the fact that, before the patch is welded to the blade 2, a start-of-run test piece is welded. For this purpose, two test piece elements, namely a first element 18, shown in FIG. 4, corresponding to the blade 2, and a second element 19, shown in FIG. 5, corresponding to the patch 11, are welded together. The first test piece element 18, corresponding to the blade 2, will be denoted by the term "first element 18" and the second test piece element 19 corresponding to the patch 11 will be denoted by the term "second element 19". The term "test piece" will correspond to the test piece once welded, that is to say to the two elements 18, 19 welded together.

The first element 18 has a cutting line 20, the profile of which is identical to the defined profile of the cutting line 10 of the blade 2. This element is made of the same material, here Ti17 titanium, which has undergone the same treatment processes as the blade 2, from its smelting right up to its use in service, and has the same surface characteristics and the same metallurgical properties and has been machined in the same way. Preferably, it may be a portion coming from the forged blisk preform, thereby assuring similarity of the characteristics. It includes portions corresponding to the heels 13, 14, even if these have not been shown.

Likewise, the second element 19 has a cutting line 21, the profile of which is identical to that of the cutting line 12 of the patch 11, and similar characteristics in the same way as previously. It includes the thickness oversize of the patch 11 and portions 22, 23 corresponding to the heels 13, 14.

The first element 18 and the second element 19 are welded together by the machine that will be used for welding the patch 11 to the blade 2, with the parameters preset for this welding. The presetting of the parameters may be obtained in the manner that we will describe below. The same holding device is used. Thus, before the patch 11 is welded to the blade 2, a very similar process of welding the two elements 18, 19 together is carried out in order to obtain the start-of-run test piece.

It is even possible, so as to weld even more representatively to the welding of the patch 11 to the blade 2, to provide means that simulate the mass and volume environment of the blade 2. This is because, owing to the mass surrounding the blade 2, especially the presence, near the blade 2, of the hub supporting the rim 3 for retaining the blades 2, a thermal pumping effect is produced during welding. The welding heat, injected into a localized sport, which is the weld bead, has a tendency to diffuse into the bulk, this diffusion varying according to the latter. The environment of the blade 2 is taken into account when welding the start-of-run test piece, which may, for example be simulated using the tooling of the holding device, which has a greater mass than that which would be necessary.

Once the two elements 18, 19 of the start-of-run test piece have been welded together, the actual start-of-run test piece is therefore obtained. The quality of the weld of the start-of-run test piece is then checked. Depending on the requirements, it is possible to carry out only visual checks or checks under a binocular microscope, or to make sections transverse and longitudinal to the joint plane so as to carry out metallurgical examinations.

If this or these checks reveal poor welding, the parameters are adapted and a further start-of-run test piece is optionally welded, and so on until a start-of-run test piece considered to be good is obtained, in which case the parameters of the machine are validated as it is considered that they correspond to the repair acceptance criteria.

Once the parameters of the machine have been validated, the patch 11 may be welded to the blade 2 in order to repair it, using the same parameters. The prior checking of a start-of-run test piece is sufficient to authorize the repair of a plurality of identical blades 2 of one and the same blisk, or even of several identical blisks.

It may be noted that the electron-beam welding machine parameters are preset. However, even though these parameters have been set so as to obtain good welding, the start-of-run test piece makes it possible to ensure that these parameters are always correct, since wear, heat, etc. affecting the precision of the machine cannot be excluded.

According to one feature of the method of the invention, after the blade or blades 2 of the blisk(s) have been repaired, an end-of-run test piece is welded. Such a test piece is identical to the start-of-run test piece described above, with the same two elements 18, 19. The welding is carried out in a completely identical manner, with the parameters validated by the checking of the start-of-run test piece, which were used for repairing the blades 2. Likewise, one or more checks are made on the end-of-run test piece, thereby making it possible to validate or not the repair of the blade or blades 2 of the blisk(s). Preferably, the end-of-run test piece is checked precisely, with, for example a metallurgical examination, in order to search for blowholes, which are cavities formed by the gas given off by the metal. In the case of Ti17 titanium, these blowholes are as small as 5 to 100 µm and cannot be detected by simple radiography. The density of micropores observed during the metallurgical inspection will be the key factor for accepting the repair. Thus, by welding a start-of-run test piece and an end-of-run test piece, and by checking them, it is possible to validate the entire run, that is to say the repair of the blisk or blisks, since if the start and the end of the runs are correct, then the entire repair or repairs is/are considered to be validated.

Preferably, the operations carried out on the blade 2 once it has been welded, (heat treatment, ultrasonic peening, etc.) are performed, where this is possible, after the welding and after the end-of-run test piece has been checked.

According to one feature of the invention, the machine parameters are preset on what are called development test pieces that are identical to the start-of-run and end-of-run test pieces. Thanks to these development test pieces, the welding machine parameters are experimentally determined for repairing a blade 2 of one particular type, with a defined profile. This development of the parameters may be carried out upon acceptance of a machine by the repairer, or else beforehand by the blisk manufacturer, who will then give the blisk repairer the parameters to be applied to the blades 2. The benefit of the start-of-run test piece(s) makes it possible even more in this case to adapt parameters which may undergo slight variations since they are not implemented on the same machine.

Thus implemented, the method of the invention makes it possible not only to repair a Ti17 titanium blisk, which was not possible in the prior art, but also to standardize such repairs. The manufacturer thus provides its repairers with the parameters to be implemented for repairing the blades 2, to carry out the welding and check one or more start-of-run test pieces in order to validate these parameters, repair one or more blades with a summary check, or even with no check, and then validate this repair by welding and checking an end-of-run test piece.

Figure 6:
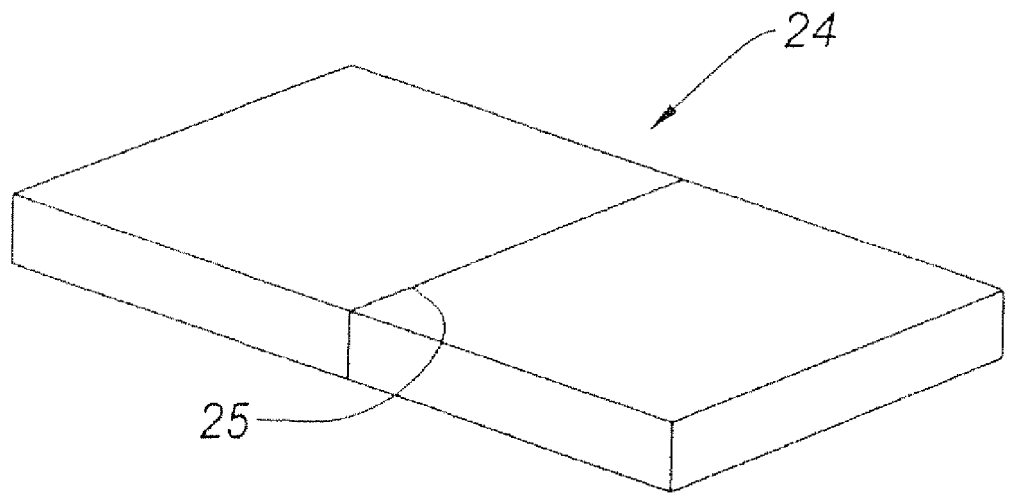
FIG. 6 shows a schematic perspective view of a test piece for validating the mechanical integrity of the weld, used for validating a machine/material pair for implementing the method of the invention.
Figure 7:
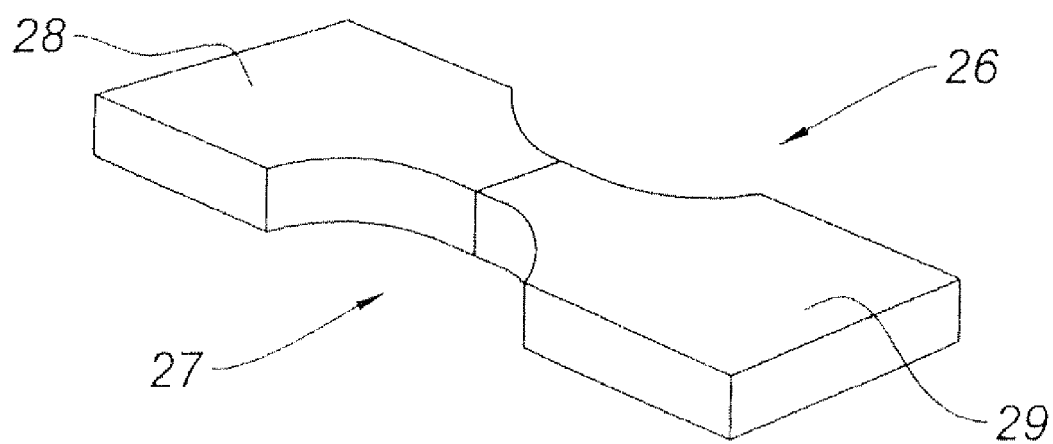
FIG. 7 shows a schematic perspective view of a test piece of FIG. 6, cut out for cyclic fatigue tests.

According to another feature of the invention, a welding machine is prevalidated by means of a test piece 24 called a mechanical-integrity validation test piece, shown in FIG. 6. For this purpose, two plates of thickness corresponding to at least the maximum thickness of the blade 2 are electron-beam welded, with preset parameters, as it is during welding of the blade that most defects are liable to be generated so as to obtain the mechanical integrity validation test piece 24 with the resulting weld line 25.

A slice 26 is then cut from the mechanical-integrity validation test piece 24, transversely to the weld line 25, machined so as to form a bar 27 in its central part that includes the weld line 25 running transversely to the bar 27. The machining is carried out so as to leave, at the ends of the bar 27, wider areas 28, 29 for being gripped by the jaws of an apparatus with which cyclic fatigue trials are carried out. Such trials employ successive tensile and compressive forces at various temperatures, for example at room temperature and at the operating temperatures of the blades 2. The test piece 24 may also be used for carrying out various checks, such as those described above, and, for example may be cut transversely and longitudinally for the purpose of metallographic examination.

Thus, the mechanical-integrity validation test piece 24 makes it possible to validate a machine/material pair and thus to define the impact of a typical repair on the material and the lowering of its mechanical properties.

Advantageously, such a mechanical-integrity validation is carried out for each machine, before the implementation of the repair method and before the welding of the start-of-run test piece. The validation is therefore not performed as for the material, but for each machine, in conjunction with the material.

The invention claimed is:

1. A method of repairing a blade of a one-piece bladed disc of a turbomachine that includes at least one damaged region by electron-beam welding of a patch using an electron-beam welding machine, comprising:

machining the at least one damaged region of the blade to obtain a region to be repaired with a defined profile along a blade cutting line;

welding a first test piece element with the defined profile to a second test piece element with the same material of the patch using the welding machine with preset operating parameters to obtain a start-of-run test piece;

checking the weld quality of the start-of-run test piece based on a predetermined repair acceptance criteria;

welding the patch on to the region to be repaired of the blade using the same electron-beam welding machine without changing the operating parameters thereof; and reworking the repaired region by machining, wherein the patch includes a profile along a patch cutting line, the patch cutting line exactly follows the blade cutting line, wherein a profile of the first test piece element is the same as the defined profile of the blade, and wherein a profile of the second test piece is the same as the profile of the patch.

2. The method according to claim 1, wherein the machining of the damaged region includes cutting out a standardized portion that includes the damaged region along the blade cutting line.

3. The method according to claim 2, wherein the patch cutting line includes a profile corresponding to the defined profile of the cutting line of the blade with a thickness oversize.

4. The method according to claim 3, wherein the thickness oversize is approximately 1 mm, divided by about 0.5 mm on each side of the cutting line, and a thickness of the blade varies between 0.5 and 6 mm.

5. The method according to claim 1, wherein the electron beam is slightly offset on the side with the patch during welding of the patch.

6. The method according to claim 1, wherein at least one heel attached to the patch is provided.

7. The method according to claim 1, further comprising, after welding the patch on to the blade, welding a third test piece element with the defined profile to a fourth test piece element, with the same material of the patch using the same electron-beam welding machine without changing the operating parameters thereof to obtain an end-of-run test piece; and checking the quality of the end-of-run test piece, wherein a profile of the third test piece element is the same as the profile of the defined profile of the blade, and wherein a profile of the fourth test piece is the same as the profile of the patch.

8. The method according to claim 7, further comprising determining the parameters of the electron-beam welding machine by the welding a fifth test piece element with the defined profile to a sixth test piece element to obtain a development test piece and testing, by at least one of non-destructive or destructive testing, the development test piece.

9. The method according to claim 8, the first, third and fifth elements, and the second, fourth and sixth elements of the start-of-run test piece of the end-of-run test piece and the development test piece, respectively, are identical.

10. The method according to claim 8, wherein the welding of a test piece is performed with means for simulating the mass environment of the blade to simulate the thermal pumping.

11. The method according to claim 1, further comprising validating the material/machine pair, during which two plates of the material of the blade, with a thickness at least equal to the maximum thickness of the defined profile of the blade, are welded to obtain a test piece for validating the mechanical integrity, and at least cyclic fatigue tests are carried out on the test piece for validating the mechanical integrity.

12. The method according to claim 1, wherein the at least one region to be repaired is at least one of blade tips, leading edge or trailing edge corners, leading edges or trailing edges of the blade.

13. The method according to claim 1, wherein the blade includes Ti17.

14. The method according to claim 1, wherein the turbomachine is a turbojet.

15. The method according to claim 1, wherein the first test element is from a portion of a forged preform of the one-piece bladed disk such the first test element has the same surface characteristics and metallurgical properties as the blade.

16. The method according to claim 1, wherein the start-of-run test piece, the blade and the patch include the same material.

17. The method according to claim 4, wherein the thickness of the blade varies between 0.7 and 3.45 mm.

18. The method according to claim 6, wherein the welding of the patch on to the region to be repaired of the blade starts on the at least one heel attached to the patch.

* * * * *